United States Patent [19]

Wilson et al.

[11] 4,075,205

[45] Feb. 21, 1978

[54] (1,3-DITHIOLO-(4,5-b) (1,2,5)THIADIAZOLO(3',4'-e)PYRAZIN-6-YLIDENE)-PROPANEDINITRILE

[75] Inventors: Charles A. Wilson; Craig E. Mixan, both of Midland, Mich.

[73] Assignee: The Dow Chemical Company, Midland, Mich.

[21] Appl. No.: 770,716

[22] Filed: Feb. 22, 1977

[51] Int. Cl.² ............................................ C07D 513/14
[52] U.S. Cl. .............................. 260/250 BC; 424/250
[58] Field of Search ................................... 260/250 BC

[56] References Cited

U.S. PATENT DOCUMENTS 3,850,929  11/1974  Tong ............................ 260/250 BC Primary Examiner—Alton D. Rollins
Assistant Examiner—James H. Turnipseed
Attorney, Agent, or Firm—Daniel L. DeJoseph; C. Kenneth Bjork

[57] ABSTRACT (1,3-Dithiolo(4,5-b) (1,2,5)thiadiazolo(3',4'-e)pyrazin-6-ylidene)-propanedinitrile is prepared by reacting di(sodiomercapto)methylenemalononitrile with 5,6-dichloro-1,2,5-thiadiazole(3,4-b)pyrazine in dimethylformamide as reaction medium at a temperature between about 20° C and about 60° C until the reaction is substantially complete. The reaction product has antimicrobial utility.

1 Claim, No Drawings

(1,3-DITHIOLO-(4,5-b)(1,2,5)THIADIAZOLO(3',4'-e)PYRAZIN-6-YLIDENE)-PROPANEDINITRILE

DESCRIPTION OF KNOWN PRIOR ART

Pyrazino-[2,3-d]-1,3-dithiole-$\Delta^{2,\alpha}$-malononitrile is disclosed in *J. Pharm. Sci.*, 57, No. 9, pp. 1611–1612 (1968). It is disclosed as having radioprotective properties.

SUMMARY OF THE INVENTION

This invention concerns the new compound (1,3-dithiolo(4,5-b)(1,2,5)thiadiazolo(3',4'-e)pyrazin-6-ylidene)-propanedinitrile, hereinafter alternatively referred to as "Compound", corresponding to the formula

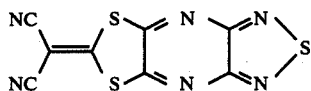

The Compound is a light yellow solid which is soluble in benzene, ethanol, methylene chloride and acetone and is insoluble in water.

The Compound is prepared by adding 5,6-dichloro-1,2,5-thiadiazole(3,4-b)pyrazine to a substantially equimolar proportion of di(sodiomercapto)methylenemalononitrile in dimethylformamide. The reaction mixture is stirred at about 20° C to about 60° C until substantial completion of the reaction; usually from about .5 to about 3 hours. Upon completion of the reaction, the mixture is poured into ice water and the crude solid product which precipitates is recovered by filtration, washed with water, and dried. The product melts at about 310° C with decomposition.

DESCRIPTION OF THE PREFERRED EMBODIMENTS

The following example and teachings illustrates the present invention and the manner by which it can be practiced but as such should not be construed as limitations upon the overall scope of the same. The product Compound is identified by elemental analysis and infrared spectrophotometry.

EXAMPLE

Preparation of (1,3-dithiolo(4,5-b)(1,2,5)-thiadiazole(3',4'-e)pyrazin-6-ylidene)-propanedinitrile To a stirred solution of 4.3 g (0.023 mol) of di(sodiomercapto)methylenemalononitrile in 100 ml of dimethylformamide (DMF) was added 4.8 (0.023 mol) of 5,6-dichloro-1,2,5-thiadiazole(3,4-b)pyrazine. The reaction mixture was stirred and heated in a water bath to 50° C for 1.5 hours and poured into 500 ml water. The resulting solid was collected by suction filtration, washed with water, and dried in vacuo to yield 5.8 g of a light yellow solid, m.p. (decomposition) 310° C. The calculated yield, from the pyrazine, was 91.2%.

Anal. Calcd. for $C_8N_6S_3$: C, 34.77; N, 3.42. Found: C, 34.32; N, 30.31.

The Compound of the invention is useful as an antimicrobial for the control of bacteria and fungi. This is not to suggest that the Compound and mixtures thereof with usual additives are equally effective against all such organisms at the same concentration. For such uses, the Compound can be employed in an unmodified form or dispersed on a finely divided solid and employed as a dust. Such mixtures can also be dispersed in water with the aid of a surface-active agent and the resulting emulsion employed as a spray. In other procedures, the Compound can be employed as the active constituents in solvent solutions, oil-in-water or water-in-oil emulsions. The augmented compositions are adapted be formulated as concentrates and subsequently diluted with additional liquid or solid adjuvants to produce the ultimate treating compositions. Good results are obtained when employing compositions containing antimicrobial concentrations and usually from about 1 to about 100 parts by weight of the Compound per million parts of such compositions.

Incorporation of the Compound of this invention into materials which are subject to fungal attack inhibits the growth of the fungi and preserves the original value of the materials. The compound is sufficiently nonvolatile and water-insoluble that it will persist on or in such materials for long periods of time. Examples of materials which are adversely affected by fungal growth are latex and alkyl paint films, wood and wooden products. The inventive Compound is sufficiently active against fungi that only small quantities are required to prevent mildew on paint films or wood rot. The compound is therefore useful for long-term protection against fungal growth in or on materials having a wood basis or a protective or decorative paint film subject to fungal attack.

In representative activity tests, the Compound is dispersed in warm melted nutrient agar which is then poured into petri dishes and allowed to solidify, the Compound being employed in an amount sufficient to provide from 0.5 to 500 parts by weight thereof per million parts (ppm) of the ultimate agar composition. The surface of the agar is then inoculated with a variety of bacterial and fungal pest oganisms, and the inoculated plates are incubated under conditions conducive to bacterial and fungal growth. Similar check plates in which the agar does not contain the Compound or other toxic compounds are similarly inoculated and incubated.

In such operations, the Compond gave 100% growth inhibition (kills) and control of the following organisms at the indicated concentrations in parts per million:

TABLE

Antimicrobial Activity of (1,3-Dithiolo(4,5-b) (1,2,5)-thiadiazolo (3',4'-e)pyrazin-6-ylidene)-propanedinitrile

| Organism | Concentration in ppm |
|---|---|
| S. aureus | 1 |
| S. typhosa | 1 |
| B. subtilis | 1 |
| C. albicans N | 0.5 |
| C. albicans D | 0.5 |
| C. pelliculosa | 0.5 |
| C. ips | 0.5 |
| Trichoderm Sp. P-42 | 5 |
| A. niger | 0.5 |
| A. fumigatus | 0.5 |
| P. chrysogesum | 0.5 |
| Torulopsis Sp. | 0.5 |
| T. mentagrophytes | 0.5 |
| A. pullulans | 0.5 |

Preparation of Starting Materials

Di(sodiomercapto)methylenemalononitrile is prepared by the method of J. D. Kendall and A. D. Edwards in U.S. Pat. No. 2,493,071 (1950). The preparation of 5,6-dichloro-1,2,5-thiadiazolo(3,4-b)pyrazine is taught by Y. C. Tong in *J. Heterocyclic Chemistry*, 12, 451 (1975).

What is claimed is:

1. The compound (1,3-Dithiolo(4,5-b)(1,2,5)-thiadiazolo(3',4'-e)pyrazin-6-ylidene)-propanedinitrile.

* * * * *

UNITED STATES PATENT AND TRADEMARK OFFICE
CERTIFICATE OF CORRECTION

PATENT NO.   : 4,075,205
DATED        : February 21, 1978
INVENTOR(S)  : Charles A. Wilson and Craig E. Mixan It is certified that error appears in the above-identified patent and that said Letters Patent are hereby corrected as shown below:

Column 1, line 59 "Anal. Calcd. for $C_8N_6S_3$: C, 34.77; N, 3.42. Found: C," should read --Anal. Calcd. for $C_8N_6S_3$: C, 34.77; N, 30.42. Found: C,--;

Column 2, line 3 "constitutents in solvent solutions, oil-in-water or water-" should read --constituent in solvent solutions, oil-in-water or water- --;

Column 2, line 5 "adapted be formulated as concentrates and subsequently" should read --adapted to be formulated as concentrates and subsequently--;

Column 2, line 21 "mildew on paint films or wood rot. The compound is" should read --mildew on paint films or wood rot. The Compound is--;

Column 2, line 33 "of bacterial and fungal pest oganisms, and the inocu-" should read --of bacterial and fungal pest organisms and the inocu- --;

Column 2, line 39 "In such operations, the Compond gave 100% growth" should read --In such operations, the Compound gave 100% growth--;

Signed and Sealed this

Tenth Day of October 1978

[SEAL]

Attest:

RUTH C. MASON
Attesting Officer

DONALD W. BANNER
Commissioner of Patents and Trademarks